United States Patent [19]
Daley et al.

[11] Patent Number: 6,010,999
[45] Date of Patent: Jan. 4, 2000

[54] STABILIZATION OF FIBROBLAST GROWTH FACTORS BY MODIFICATION OF CYSTEINE RESIDUES

[75] Inventors: Michael Joseph Daley; Brian Lee Buckwalter; Susan Mancini Cady, all of Yardley; Hong-Ming Shieh, Langforne, all of Pa.; Peter Bohlen, Peekskill; Andrew P. Seddon, Monroe, both of N.Y.

[73] Assignee: American Cyanamid Company, Madison, N.J.

[21] Appl. No.: 08/459,906

[22] Filed: Jun. 2, 1995

Related U.S. Application Data

[62] Division of application No. 08/383,621, Feb. 6, 1995, which is a continuation of application No. 07/766,142, Sep. 25, 1991, abandoned, which is a continuation-in-part of application No. 07/519,047, May 4, 1990, abandoned.

[30] Foreign Application Priority Data

Apr. 18, 1991 [EP] European Pat. Off. ............ 91106224

[51] Int. Cl.[7] .......................... A01N 61/00; A01N 37/18
[52] U.S. Cl. ................. 514/2; 514/12; 530/399; 530/402; 530/408; 530/409
[58] Field of Search ..................... 530/399, 402, 530/408, 409; 514/12, 2

[56] References Cited

U.S. PATENT DOCUMENTS

| | | | |
|---|---|---|---|
| 4,179,337 | 12/1979 | Davis et al. | 435/181 |
| 4,732,863 | 3/1988 | Tomasi et al. | 436/547 |
| 4,766,106 | 8/1988 | Katre et al. | |
| 4,847,325 | 7/1989 | Shadle et al. | 525/54.1 |
| 5,037,806 | 8/1991 | Krivi. | |
| 5,153,265 | 10/1992 | Shadle et al. | 525/54.1 |
| 5,166,322 | 11/1992 | Shaw et al. | 530/351 |
| 5,183,660 | 2/1993 | Ikeda et al. | 424/94.3 |
| 5,206,344 | 4/1993 | Katre et al. | 530/351 |
| 5,217,954 | 6/1993 | Foster et al. | |
| 5,223,483 | 6/1993 | Thomas et al. | 514/12 |
| 5,302,702 | 4/1994 | Seddon et al. | |
| 5,310,883 | 5/1994 | Seddon et al. | 530/399 |

FOREIGN PATENT DOCUMENTS 0 355 460  2/1990  European Pat. Off. .

OTHER PUBLICATIONS

Veronese et al. J. Pharm. Phamacol. 35: 757–758, 1983.

*Primary Examiner*—Lila Feisee
*Assistant Examiner*—Christine Saoud
*Attorney, Agent, or Firm*—Anne M. Rosenblum

[57] ABSTRACT

The present invention relates to physiologically-active derivatized natural and recombinant mammalian and human proteins and polypeptides. The invention provides chemical methods for derivatizing natural and recombinantly-derived proteins or polypeptides containing cysteine residues, either naturally or through site specific mutageneses. The pharmaceutical compositions containing said derivatized proteins and/or polypeptides are formulated to provide stable, long-acting compositions of such proteins and/or polypeptides, previously difficult to achieve.

6 Claims, 2 Drawing Sheets

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO:1:

```
Met Asp Gln Phe Pro Ala Met Pro Leu Ser Ser Leu Phe Ala Asn Ala
 1               5                  10                  15

Val Leu Arg Ala Gln His Leu His Gln Leu Ala Ala Asp Thr Tyr Lys
                20                  25                  30

Glu Phe Glu Arg Ala Tyr Ile Pro Glu Gly Gln Arg Tyr Ser Ile Gln
            35                  40                  45

Asn Ala Gln Ala Ala Phe Cys Phe Ser Glu Thr Ile Pro Ala Pro Thr
         50                  55                  60

Gly Lys Asp Glu Ala Gln Gln Arg Ser Asp Val Glu Leu Leu Arg Phe
 65                  70                  75                  80

Ser Leu Leu Leu Ile Gln Ser Trp Leu Gly Pro Val Gln Phe Leu Ser
                85                  90                  95

Arg Val Phe Thr Asn Ser Leu Val Phe Gly Thr Ser Asp Arg Val Tyr
               100                 105                 110

Glu Lys Leu Lys Asp Leu Glu Glu Gly Ile Gln Ala Leu Met Arg Glu
           115                 120                 125

Leu Glu Asp Gly Ser Pro Arg Ala Gly Gln Ile Leu Lys Gln Thr Tyr
           130                 135                 140

Asp Lys Phe Asp Thr Asn Leu Arg Ser Asp Asp Ala Leu Leu Lys Asn
145                 150                 155                 160

Tyr Gly Leu Leu Ser Cys Phe Lys Lys Asp Leu His Lys Ala Glu Thr
               165                 170                 175
```

```
Tyr Leu Arg Val Met Lys Cys Arg Arg Phe Val Glu Ser Ser Cys Ala
            180                 185                 190
Phe (2) INFORMATION FOR SEQ ID NO:2:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO:2:

Met Asp Gln Phe Pro Ala Met Ser Leu Ser Gly Leu Phe Ala Asn Ala
1               5                   10                  15

Val Leu Arg Ala Gln His Leu His Gln Leu Ala Ala Asp Thr Phe Lys
            20                  25                  30

Glu Phe Glu Arg Thr Tyr Ile Pro Glu Gly Gln Arg Tyr Ser Ile Gln
        35                  40                  45

Asn Thr Gln Val Ala Phe Cys Phe Ser Glu Thr Ile Pro Ala Pro Thr
    50                  55                  60

Gly Lys Asn Glu Ala Gln Gln Lys Ser Asp Leu Glu Leu Leu Arg Ile
65                  70                  75                  80

Ser Leu Leu Leu Ile Gln Ser Trp Leu Gly Pro Leu Gln Phe Leu Ser
                85                  90                  95

Arg Val Phe Thr Asn Ser Leu Val Phe Gly Thr Ser Asp Arg Val Tyr
            100                 105                 110

Glu Lys Leu Lys Asp Leu Glu Glu Gly Ile Leu Ala Leu Met Arg Glu
        115                 120                 125

Leu Glu Asp Gly Thr Pro Arg Ala Gly Gln Ile Leu Lys Gln Thr Tyr
    130                 135                 140

Asp Lys Phe Asp Thr Asn Met Arg Ser Asp Asp Ala Leu Leu Lys Asn
145                 150                 155                 160

Tyr Gly Leu Leu Ser Cys Phe Arg Lys Asp Leu His Lys Thr Glu Thr
                165                 170                 175

Tyr Leu Arg Val Met Lys Cys Arg Arg Phe Gly Glu Ala Ser Cys Ala
            180                 185                 190

Phe (2) INFORMATION FOR SEQ ID NO:3:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO:3:

Met Asp Gln Phe Pro Ala Met Pro Leu Ser Ser Leu Phe Ala Asn Ala
1               5                   10                  15

Val Leu Arg Ala Gln His Leu His Gln Leu Ala Ala Asp Thr Tyr Lys
            20                  25                  30

Glu Phe Glu Arg Thr Tyr Ile Pro Glu Gly Gln Arg Tyr Ser Ile Gln
        35                  40                  45

Asn Ala Gln Ala Ala Phe Cys Phe Ser Glu Thr Ile Pro Ala Pro Thr
    50                  55                  60

Gly Lys Asp Glu Ala Gln Gln Arg Ser Asp Val Glu Leu Leu Arg Phe
```

```
          65                  70                  75                  80
Ser Leu Leu Leu Ile Gln Ser Trp Leu Gly Pro Val Gln Phe Leu Ser
                        85                  90                  95

Arg Val Phe Thr Asn Cys Leu Val Phe Gly Thr Ser Asp Arg Val Cys
                100                 105                 110

Glu Lys Leu Lys Asp Leu Glu Glu Gly Ile Gln Ala Leu Met Arg Glu
            115                 120                 125

Leu Glu Asp Gly Ser Pro Arg Ala Gly Gln Ile Leu Lys Gln Thr Tyr
        130                 135                 140

Asp Lys Phe Asp Thr Asn Leu Arg Ser Asp Asp Ala Leu Leu Lys Asn
145                 150                 155                 160

Tyr Gly Leu Leu Ser Cys Phe Arg Lys Asp Leu His Lys Thr Glu Thr
                165                 170                 175

Tyr Leu Arg Val Met Lys Glu Arg Arg Phe Val Glu Ser Ser Glu Ala
                180                 185                 190

Phe
```

(2) INFORMATION FOR SEQ ID NO:4:

(i) SEQUENCE CHARACTERISTICS:
        (A) LENGTH: 194 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp Gln Phe Pro Thr Ile Pro Leu Ser Arg Leu Phe Asp Asn Ala
1                   5                   10                  15

Met Leu Arg Ala His Arg Leu His Gln Leu Ala Phe Asp Thr Tyr Gln
                20                  25                  30

Glu Phe Glu Glu Ala Tyr Ile Pro Lys Glu Gln Lys Tyr Ser Phe Leu
            35                  40                  45

Gln Asn Pro Gln Thr Ser Leu Cys Phe Ser Glu Ser Ile Pro Thr Pro
        50                  55                  60

Ser Asn Arg Glu Glu Thr Gln Gln Lys Ser Asn Leu Glu Leu Leu Arg
65                  70                  75                  80

Ile Ser Leu Leu Leu Ile Gln Ser Trp Leu Glu Pro Val Gln Phe Leu
                        85                  90                  95

Arg Ser Val Phe Ala Asn Ser Leu Val Tyr Gly Ala Ser Asp Ser Asn
                100                 105                 110

Val Tyr Asp Leu Leu Lys Asp Leu Glu Glu Gly Ile Gln Thr Leu Met
            115                 120                 125

Gly Arg Leu Glu Asp Gly Ser Pro Arg Thr Gly Gln Ile Phe Lys Gln
        130                 135                 140

Thr Tyr Ser Lys Phe Asp Thr Asn Ser His Asn Asp Asp Ala Leu Leu
145                 150                 155                 160

Lys Asn Tyr Gly Leu Leu Tyr Cys Phe Arg Lys Asp Met Asp Lys Val
                165                 170                 175

Glu Thr Phe Leu Arg Ile Val Gln Cys Arg Ser Val Glu Gly Ser Cys
                180                 185                 190

Gly Phe
```

(2) INFORMATION FOR SEQ ID NO:5:

(i) SEQUENCE CHARACTERISTICS:
        (A) LENGTH: 135 amino acids

```
            (B) TYPE: amino acid
            (D) TOPOLOGY: linear (ii) MOLECULE TYPE: protein (xi) SEQUENCE DESCRIPTION: SEQ ID NO:5:

Ala Pro Thr Ser Ser Thr Gly Asn Thr Met Lys Glu Val Lys Ser
1               5                   10                  15

Leu Leu Leu Asp Leu Gln Leu Leu Glu Lys Val Lys Asn Pro Glu
                20                  25                  30

Asn Leu Lys Leu Ser Arg Met His Thr Phe Asp Phe Tyr Val Pro Lys
            35                  40                  45

Val Asn Ala Thr Glu Leu Lys His Leu Lys Cys Leu Leu Glu Glu Leu
    50                  55                  60

Lys Leu Leu Glu Glu Val Leu Asn Leu Ala Pro Ser Lys Asn Leu Asn
65                  70                  75                  80

Pro Arg Glu Ile Lys Asp Ser Met Asp Asn Ile Lys Arg Ile Val Leu
            85                  90                  95

Glu Leu Gln Gly Ser Glu Thr Arg Phe Thr Cys Glu Tyr Asp Asp Ala
                100                 105                 110

Thr Val Asn Ala Val Glu Phe Leu Asn Lys Trp Ile Thr Phe Cys Gln
        115                 120                 125

Ser Ile Tyr Ser Thr Met Thr
        130             135

(2) INFORMATION FOR SEQ ID NO:6:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

TTCACCAACT GTCTGGTGTT T                                         21

(2) INFORMATION FOR SEQ ID NO:7:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

GACCGCGTCT GTGAGAAGCT G                                         21

(2) INFORMATION FOR SEQ ID NO:8:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO
```

(iv) ANTI-SENSE: NO (xi) SEQUENCE DESCRIPTION: SEQ ID NO:8:

AGCTTACCTG CCATGGCAGC CGGGAGCATC ACCACGCTGC CCGCCCTT            48

(2) INFORMATION FOR SEQ ID NO:9:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

AGCTTCATAT GGCAGCCGGG AGCATCACCA CGCTGCCCGC CCTT               44

(2) INFORMATION FOR SEQ ID NO:10:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

AGCTTCATAT GGCAGCCGGG AGCATCACCA CGCTGCCCGC CCTT               44

(2) INFORMATION FOR SEQ ID NO:11:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

AGCTTCATAT GGCTGAAGGG GAAATCACCA CGCTGCCCGC CCTT               44

STABILIZATION OF FIBROBLAST GROWTH FACTORS BY MODIFICATION OF CYSTEINE RESIDUES

This a divisional of copending application Ser. No. 08/383,621, filed on Feb. 6, 1995 which is a continuation of application Ser. No. 07/766,142, filed on Sep. 25, 1991, now abandoned, which, in turn, is a continuation-in-part of application Ser. No. 07/519,047, filed on May 4, 1990, now abandoned.

BACKGROUND OF THE INVENTION

The present invention relates to novel derivatized recombinant or natural proteins and/or polypeptides wherein if said protein and/or polypeptide contains one or more cysteine residue, said residue is derivatized with substituents as herein defined. Further, proteins not containing a cysteine in their natural forms can be altered, via site specific mutagenesis techniques, for instance, in order to introduce cysteines at advantageous sites and thereafter derivatize said cysteine(s).

Although molecular biological techniques have dramatically increased the availability of many proteins and/or polypeptides (hereinafter referred to as proteins), the therapeutic use of said proteins is often times hindered by other factors, such as aggregation, proteolytic degradation, poor bioavailability and physical properties which preclude efficient formulations. In the present invention the highly reactive sulfhydryl groups on cysteine residues within both recombinantly-derived and naturally-derived proteins are derivatized to modify the effective charge on the protein surface, and thereby the isoelectric point, or to link a surface-modifying polymer to the protein.

The advantage of modifying the charge iso-electric point is well known due to the minimization of protein aggregation if the pH of a protein formulation is significantly different than the iso-electric point. Manipulation of the iso-electric point, therefore, affords a technique to minimize aggregation.

Also, another mechanism for enhancing protein formulation is by conjugation of the protein with derivatizing compounds, which include, but are not limited to, polyethylene glycol and polypropylene glycol. Some of these benefits recognized include: lowered immunogenicity and antigenicity, increased duration of action, and altered pharmacokinetic properties. [F. M. Veronese, Chimicaoggi (1989) 53].

Heretofore, attachment of polymeric molecules to proteins was principally through lysine or other basic amino acids. This was accomplished with alkylating agents such as triazine derivatives, diazonium salts or active acylating agents such as succinic acid derivatives. These reactions were difficult to control and significant losses in biological activity occurred frequently due to reactions with essential amino acids in the proteins [see F. F. Davis et al Polymer (1979) 20 357].

In contrast, the present invention provides a selective method for modifying the less abundant cysteine residues either naturally occurring within a protein or incorporated within a protein by such methods as site specific mutagenesis.

It is an object of the present invention to provide compositions of derivatized proteins, which proteins include but are not limited to the (mammalian, avian and fish) somatotropins, mammalian IGF-1 and IGF-2, interleukins and interferons, prourokinase, tumor necrosis factor other growth factors such as fibroblast growth factor and antithrombin III which are biologically effective and yet stable to administer. Furthermore, as previously indicated, said proteins are not limited to those proteins which in their natural form contain cysteine residue(s) since site specific mutagenesis techniques are used to introduce cysteine at advantageous sites within said proteins. It is another object of the present invention to provide compositions of biologically active recombinant and/or natural proteins which are suitable for parenteral administration, said compositions comprising a biologically active amount of a derivatized somatotropin (animal or human form) or other protein or pharmaceutically and pharmacologically acceptable salt thereof in a pharmaceutically and pharmacologically acceptable solid or liquid carrier.

It is a further object of the present invention to provide novel compositions which will allow the modification of any cysteine-containing proteins. By judicious selection of the nature and number of ionizable-functional groups and/or the size and nature of the surface-modifying polymer a range of derivatized proteins with distinctly different physical properties are produced.

These and other objects of the invention will become more apparent by the more detailed description of the invention provided hereinbelow.

Figure 1:
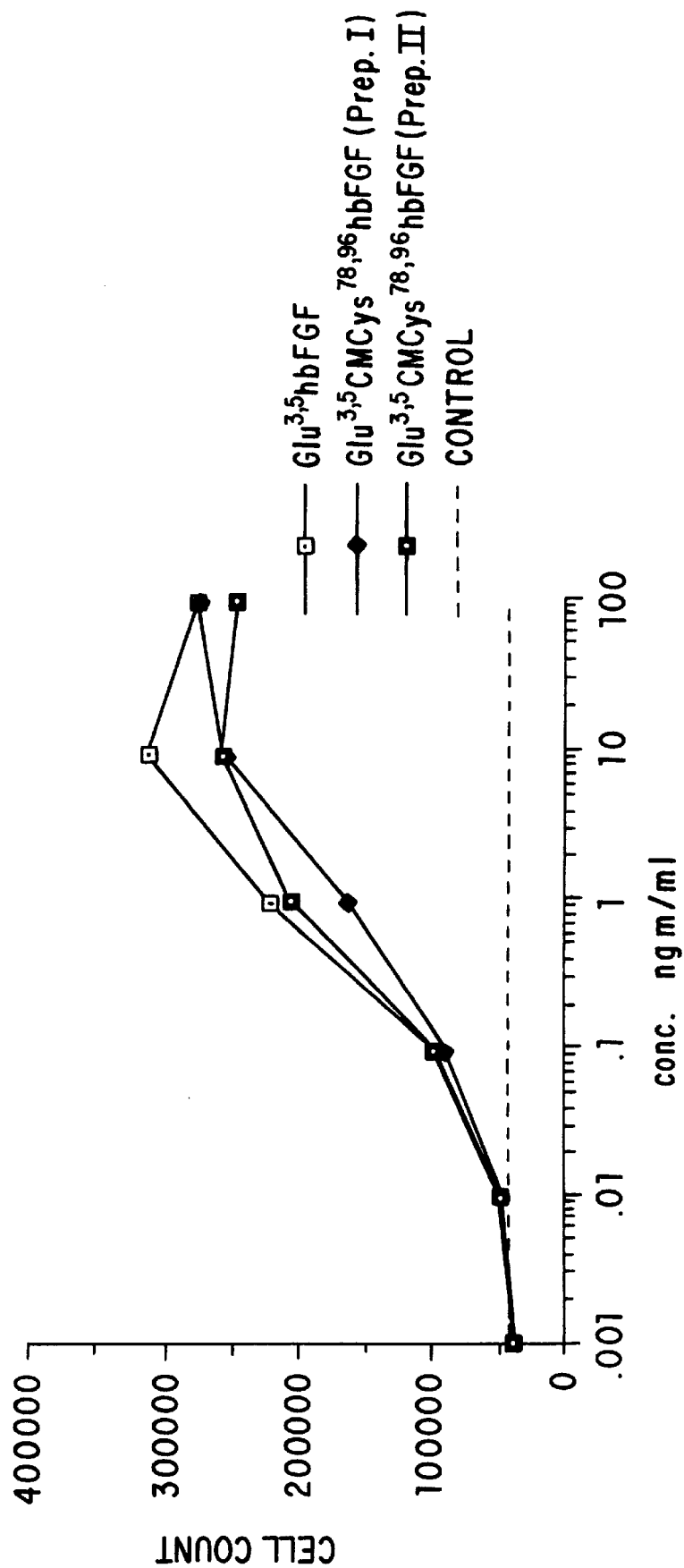
FIG. 1

Comparison of the mitogenic activities of 2 different preparations of $Glu^{3,5}$ $CMCys^{78,96}$ to $Glu^{3,5}hbFGF$ on bovine aortic arch endothelial cells.

FIG. 2

Acid Stabilities of $Glu^{3,5}$ $CMCys^{78,96}$ and $Glu^{3,5}hbFGF$. bFGF's at 10 µg/ml in 50 mM sodium acetate buffer pH 4 are incubated at 37°. Portions are withdrawn at the indicated times and assayed for mitogenic activity at fixed does of 2 ng/ml.

FIG. 3

Mitogenic activities of PEG-FGF's compared to unmodified bFGF. FGF's are assayed at 0.1,1 and 10 ng/ml.

SUMMARY OF THE INVENTION

The present invention relates to novel derivatized recombinant or natural proteins which including, but not limited to somatotropins, IGF-1 and IGF-2, interleukins, interferons, prourokinase, tumor necrosis factor growth factors such as fibroblast growth factor, epidermal-derived growth factor, inculin-derived growth factor, platelet-derived growth factor and others, and antithrombin III, wherein at least one-naturally-occurring or incorporated cysteine residue within the protein is derivatized with substituents selected from $(CH_2CO_2R_1)$, $(CH_2CONHR_1)$, $[CH(COR_2)(CH_2)_x(COR_3)]$, $[CH_2—CONHCH(COR_2)(CH_2)_x(COR_3)]$, or $[CH_2CONH(CH_2)_xCOR_4]$; wherein $R_1$ is $CH_2CH_2—(OCH_2CH_2)_yOMe$; $R_2$ and $R_3$ are OH or $R_4$; $R_4$ is $NHCH_2CH_2(OCH_2CH_2)_yOMe$ or $OCH_2CH_2(OCH_2CH_2)_yOMe$; X is an integer of from 1 to 3 and Y is an integer of from 10 to 300; with the proviso that $R_2$ and $R_3$ cannot simultaneously be OH; provided that if the derivatized cysteine residue(s) of said protein formed a disulfide linkage prior to derivatization, both cysteines will bear the same sulfhydryl derivatives after the derivatization procedure is complete. Furthermore, with some proteins containing more than one disulfide bond, it is possible to selectively cleave one or more of said disulfide bonds and those disulfide bonds which are selectively cleaved may be derivatized without affecting the remaining cysteine residues. When disulfides sequentially are cleaved it is possible to derivatize different cysteines with more than one composition. Furthermore, when said protein possesses an unpaired cysteine, that residues is derivatized without a reductive step.

The present invention also provides novel derivatizing compounds to said compounds comprising the following: $ZCH_2CO_2R_1$, $ZCH_2CONHCH(COR_2)[(CH_2)_x(COR_3)]$, $ZCH(COR_2)[(CH_2)_x(COR_3)]$ or $ZCH_2CONH(CH_2)_xCOR_2$ wherein $R_1$ is $CH_2CH_2(OCH_2CH_2)_yOMe$; $R_2$ and $R_3$ are OH or $R_4$; $R_4$ is $NHCH_2CH_2(OCH_2CH_2)_yOMe$ or $OCH_2CH_2(OCH_2CH_2)_yOMe$; Z is Br or I; X is an integer of from 1 to 3 and Y is an integer of from 10 to 300; with the proviso that $R_2$ and $R_3$ can not simultaneously be OH.

This invention further relates to a method for inhibiting aggregation of a recombinant animal somatotropin, by reducing at least one of the two disulfide bridges between the cysteine amino acid residues at the 55 and 166 positions or at the 183 and 191 positions of said somatotropins and thereafter derivatizing each of the cysteines of the reduced bridge or bridges at the 55 and 166 positions and/or at the 183 and 191 positions with the same derivative, provided that the derivatives on the cysteines at the 55 and 166 positions are the same or different substituents than the substituents on the cysteines at the 183 and 191 positions. The substituents employed in the preparation of the novel derivatized recombinant animal somatotropins of this invention include the following: $(CH_2CO_2R_1)$, $(CH_2CONHR_1)$ $[CH(COR_2)(CH_2)_x—(COR_3)]$, $[CH_2CONHCH(COR_2)(CH_2)_x(COR_3)]$, or $[CH_2CONH—(CH_2)_xCOR_4]$; wherein $R_1$ is $CH_2CH_2(OCH_2CH_2)_yOMe$; $R_2$ and $R_3$ are OH or $R_4$; $R_4$ is $NHCH_2CH_2(OCH_2CH_2)_yOMe$ or $OCH_2CH_2—(OCH_2CH_2)_yOMe$; X is an integer of from 1 to 3 and Y is an integer of from 10 to 300; with the proviso that $R_2$ and $R_3$ can not simultaneously be OH.

This invention further relates to a method to increase the half life of interleukin-2 by derivitizing the free cysteine at position 127 with the aforementioned derivatives.

In accordance with the present invention, the preferred novel animal somatotropins are recombinant porcine, bovine, ovine, human, avian and fish somatotropins wherein the disulfide bridge in the small loop of the somatotropin is reduced and the cysteines at the 183 and 191 positions derivatized with a substituent selected from $(CH_2COR_1)$, $[CH_2CONHCH(COR_2)(CH_2)_x(COR_3)]$, or $[CH_2CONH(CH_2)_xCOR_4]$; wherein $R_1$, $R_2$, $R_3$, and X are as described.

Furthermore, another novel protein of the present invention is an animal somatotropin derivative in which cysteine residues are substituted for the Ser and Tyr residues at the 102 and 112 positions respectively and in which glutamic acid has been substituted for the cysteine residues which normally occur at positions 183 and 191. This protein is produced by site specific mutagenesis techniques which are well known to those skilled in the art. Furthermore, these techniques are utilized with other proteins to introduce a tethering site for polymers which does not interfere with or alter the ability of the hormone to interact with a binding site or to elicit a biological effect.

All of the plasmids, DNA sequences and microorganisms deposited in connection with the present patent application, except where specified to the contrary, are deposited in American Cyanamid Company culture collection maintained in Princeton, N.J. and are deposited with the American Type Culture Collection (ATCC), 10801 University Boulevard, Manassas, Virginia 20110-2209 USA.

DETAILED DESCRIPTION OF THE INVENTION

Preferred modified recombinant animal proteins of this invention include but not limited to animal and human somatotropins, interleukins and interferons, as illustrated hereinbelow. Recombinantly-derived somatotropins without the additional Asp-Gln additional substitutions or with other substitutions are prepared in accordance with the present invention, as well. Further animal proteins with deletions in amino acid chain length, additions to amino acid chain length, replacement of amino acids, (additional cysteines for derivatization), fragments with the active portion and the like are all within the scope of the present invention. Further, both animal and human growth factors have been found to benefit from the derivatization contemplated by the present invention. One example is fibroblast growth factor (FGF).

Recombinant Porcine Somatotropin    (SEQ ID NO:1)

H-Met-Asp-Gln-Phe-Pro-Ala-Met-Pro-Leu-Ser-Ser-

Leu-Phe-Ala-Asn-Ala-Val-Leu-Arg-Ala-Gln-His-Leu-

His-Gln-Leu-Ala-Ala-Asp-Thr-Tyr-Lys-Glu-Phe-Glu-

Arg-Ala-Tyr-Ile-Pro-Glu-Gly-Gln-Arg-Tyr-Ser-Ile-

55
Gln-Asn-Ala-Gln-Ala-Ala-Phe-Cys-Phe-Ser-Glu-Thr-

Ile-Pro-Ala-Pro-Thr-Gly-Lys-Asp-Glu-Ala-Gln-Gln-

Arg-Ser-Asp-Val-Glu-Leu-Leu-Arg-Phe-Ser-Leu-Leu-

Leu-Ile-Gln-Ser-Trp-Leu-Gly-Pro-Val-Gln-Phe-Leu-

Ser-Arg-Val-Phe-Thr-Asn-Ser-Leu-Val-Phe-Gly-Thr-

Ser-Asp-Arg-Val-Tyr-Glu-Lys-Leu-Lys-Asp-Leu-Glu-

Glu-Gly-Ile-Gln-Ala-Leu-Met-Arg-Glu-Leu-Glu-Asp-

Gly-Ser-Pro-Arg-Ala-Gly-Gln-Ile-Leu-Lys-Gln-Thr-

Tyr-Asp-Lys-Phe-Asp-Thr-Asn-Leu-Arg-Ser-Asp-Asp-

166
Ala-Leu-Leu-Lys-Asn-Tyr-Gly-Leu-Leu-Ser-Cys-Phe-

Lys-Lys-Asp-Leu-His-Lys-Ala-Glu-Thr-Tyr-Leu-Arg- 183                              191
Val-Met-Lys-Cys-Arg-Arg-Phe-Val-Glu-Ser-Ser-Cys-

Ala-Phe-OH.

Recombinant Bovine Somatotropin    (SEQ ID NO:2)

H-Met-Asp-Gln-Phe-Pro-Ala-Met-Ser-Leu-Ser-Gly-

Leu-Phe-Ala-Asn-Ala-Val-Leu-Arg-Ala-Gln-His-Leu-

His-Gln-Leu-Ala-Ala-Asp-Thr-Phe-Lys-Glu-Phe-Glu-

Arg-Thr-Tyr-Ile-Pro-Glu-Gly-Gln-Arg-Tyr-Ser-Ile-

55
Gln-Asn-Thr-Gln-Val-Ala-Phe-Cys-Phe-Ser-Glu-Thr-

Ile-Pro-Ala-Pro-Thr-Gly-Lys-Asn-Glu-Ala-Gln-Gln-

Lys-Ser-Asp-Leu-Glu-Leu-Leu-Arg-Ile-Ser-Leu-Leu-

Leu-Ile-Gln-Ser-Trp-Leu-Gly-Pro-Leu-Gln-Phe-Leu-

Ser-Arg-Val-Phe-Thr-Asn-Ser-Leu-Val-Phe-Gly-Thr-

```
Ser-Asp-Arg-Val-Tyr-Glu-Lys-Leu-Lys-Asp-Leu-Glu-

Glu-Gly-Ile-Leu-Ala-Leu-Met-Arg-Glu-Leu-Glu-Asp-

Gly-Thr-Pro-Arg-Ala-Gly-Gln-Ile-Leu-Lys-Gln-Thr-

Tyr-Asp-Lys-Phe-Asp-Thr-Asn-Met-Arg-Ser-Asp-Asp-
                                            166
Ala-Leu-Leu-Lys-Asn-Tyr-Gly-Leu-Leu-Ser-Cys-Phe-

Arg-Lys-Asp-Leu-His-Lys-Thr-Glu-Thr-Tyr-Leu-Arg-
         183                               191
Val-Met-Lys-Cys-Arg-Arg-Phe-Gly-Glu-Ala-Ser-Cys-

Ala-Phe-OH.

Recombinant Cys¹¹², ¹²²,           (SEQ ID NO:3)

Glu¹⁸³, ¹⁹¹ porcine somatotropin

H-Met-Asp-Gln-Phe-Pro-Ala-Met-Pro-Leu-Ser-Ser-

Leu-Phe-Ala-Asn-Ala-Val-Leu-Arg-Ala-Gln-His-Leu-

His-Gln-Leu-Ala-Ala-Asp-Thr-Tyr-Lys-Glu-Phe-Glu-

Arg-Thr-Tyr-Ile-Pro-Glu-Gly-Gln-Arg-Tyr-Ser-Ile-

Gln-Asn-Ala-Gln-Ala-Ala-Phe-Cys-Phe-Ser-Glu-Thr-

Ile-Pro-Ala-Pro-Thr-Gly-Lys-Asp-Glu-Ala-Gln-Gln-

Arg-Ser-Asp-Val-Glu-Leu-Leu-Arg-Phe-Ser-Leu-Leu-

Leu-Ile-Gln-Ser-Trp-Leu-Gly-Pro-Val-Gln-Phe-Leu-
                                 112
Ser-Arg-Val-Phe-Thr-Asn-Cys-Leu-Val-Phe-Gly-Thr-
                                 122
Ser-Asp-Arg-Val-Cys-Glu-Lys-Leu-Lys-Asp-Leu-Glu-

Glu-Gly-Ile-Gln-Ala-Leu-Met-Arg-Glu-Leu-Glu-Asp-

Gly-Ser-Pro-Arg-Ala-Gly-Gln-Ile-Leu-Lys-Gln-Thr-

Tyr-Asp-Lys-Phe-Asp-Thr-Asn-Leu-Arg-Ser-Asp-Asp-

Ala-Leu-Leu-Lys-Asn-Tyr-Gly-Leu-Leu-Ser-Cys-Phe-

Arg-Lys-Asp-Leu-His-Lys-Thr-Glu-Thr-Tyr-Leu-Arg-
         183                               191
Val-Met-Lys-Glu-Arg-Arg-Phe-Val-Glu-Ser-Ser-Glu-

Ala-Phe-OH.

Recombinant Human Somatotropin     (SEQ ID NO:4)

H-Met-Asp-Gln-Phe-Pro-Thr-Ile-Pro-Leu-Ser-Arg-

Leu-Phe-Asp-Asn-Ala-Met-Leu-Arg-Ala-His-Arg-Leu-

His-Gln-Leu-Ala-Phe-Asp-Thr-Tyr-Gln-Glu-Phe-Glu-

Glu-Ala-Tyr-Ile-Pro-Lys-Glu-Gln-Lys-Tyr-Ser-Phe-
                                          56
Leu-Gln-Asn-Pro-Gln-Thr-Ser-Leu-Cys-Phe-Ser-Glu-

Ser-Ile-Pro-Thr-Pro-Ser-Asn-Arg-Glu-Glu-Thr-Gln-

Gln-Lys-Ser-Asn-Leu-Glu-Leu-Leu-Arg-Ile-Ser-Leu-

Leu-Leu-Ile-Gln-Ser-Trp-Leu-Glu-Pro-Val-Gln-Phe-

Leu-Arg-Ser-Val-Phe-Ala-Asn-Ser-Leu-Val-Tyr-Gly-

Ala-Ser-Asp-Ser-Asn-Val-Tyr-Asp-Leu-Leu-Lys-Asp-

Leu-Glu-Glu-Gly-Ile-Gln-Thr-Leu-Met-Gly-Arg-Leu-

Glu-Asp-Gly-Ser-Pro-Arg-Thr-Gly-Gln-Ile-Phe-Lys-

Gln-Thr-Tyr-Ser-Lys-Phe-Asp-Thr-Asn-Ser-His-Asn-

Asp-Asp-Ala-Leu-Leu-Lys-Asn-Tyr-Gly-Leu-Leu-Tyr-
                                       167
Cys-Phe-Arg-Lys-Asp-Met-Asp-Lys-Val-Glu-Thr-Phe-
                                   184
Leu-Arg-Ile-Val-Gln-Cys-Arg-Ser-Val-Glu-Gly-Ser-
191
Cys-Gly-Phe-OH.

Recombinant IL-2                   (SEQ ID NO:5)

H-Ala-Pro-Thr-Ser-Ser-Ser-Thr-Gly-Asn-Thr-Met-Lys-

Glu-Val-Lys-Ser-Leu-Leu-Leu-Asp-Leu-Gln-Leu-Leu-

Leu-Glu-Lys-Val-Lys-Asn-Pro-Glu-Asn-Leu-Lys-Leu-

Ser-Arg-Met-His-Thr-Phe-Asp-Phe-Tyr-Val-Pro-Lys-

Val-Asn-Ala-Thr-Glu-Leu-Lys-His-Leu-Lys-Cys-Leu-

Leu-Glu-Glu-Leu-Lys-Leu-Leu-Glu-Glu-Val-Leu-Asn-

Leu-Ala-Pro-Ser-Lys-Asn-Leu-Asn-Pro-Arg-Glu-Ile-

Lys-Asp-Ser-Met-Asp-Asn-Ile-Lys-Arg-Ile-Val-Leu-

Glu-Leu-Gln-Gly-Ser-Glu-Thr-Arg-Phe-Thr-Cys-Glu-

Tyr-Asp-Asp-Ala-Thr-Val-Asn-Ala-Val-Glu-Phe-Leu-

Asn-Lys-Trp-Ile-Thr-Phe-Cys-Gln-Ser-Ile-Tyr-Ser-

Thr-Met-Thr.
```

Derivatized Proteins

Derivatized proteins are prepared by dissolution or dispersion of protein in water or an aqueous solution of guanidine hydrochloride, sodium bicarbonate or the like, which is adjusted to pH 8.4 with an aqueous base, such as sodium or ammonium hydroxide. If reduction of a disulfide linkage is required, a dithiotheritol, i.e. (DL-threo-1, 4-dimercapto-2,3-butanediol DTT) slowly is then added to this solution. The addition is generally conducted under an atmosphere of nitrogen at room temperature. To the resulting solution is added the derivatizing agent. The mixture is stirred for about one to four hours. Progress of the reaction is monitored by Ellman titration of unmodified thiol groups or by gel electrophoresis. After the reaction is complete, it is desalted by ultrafiltration. The solution is concentrated and then subjected to several cycles of redilution with water, aqueous guanidine hydrochloride or the like, followed by ultrafiltration. The residue from the final filtration is then lyophilized to yield the derivatized protein.

The preparation of two of the derivatizing agents proceeds from N-Fmoc-Asp($^t$bu)OH and is depicted in Flow Chart 1 and Flow Chart 2. The amine derived from a polyethylene glycol monomethyl ether (PEG-OMe) is readily available using standard methodology. This amine is condensed with N-Fmoc-Asp($^t$bu)OH using dicyclohexylcarbodiimide (DCC) or other related dehydrating agent. Removal of the Fmoc protecting group utilizing standard protocols affords (I). Condensation of (I) with iodoacetic acid is effected with DCC followed by removal of the tert-butyl ester affording the alkylating agent. It is readily apparent that similar derivatives in which the polymer is attached to only the β-carboxyl or both the α and β carboxyl groups are prepared depending upon the starting material used.

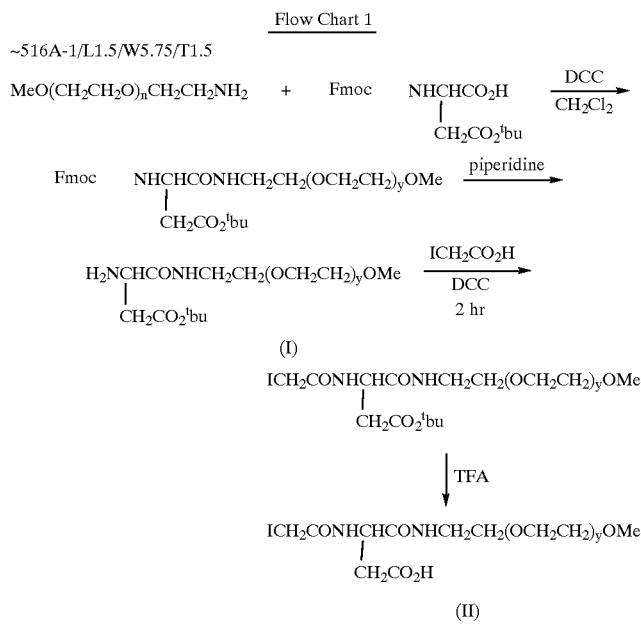

The succinic acid derivative (Flow Chart II) also is prepared from N-Fmoc-Asp($^t$bu)OH. The free acid is converted into the p-nitrobenzoate (PNB) ester with DCC and the amino group deprotected with piperidine.

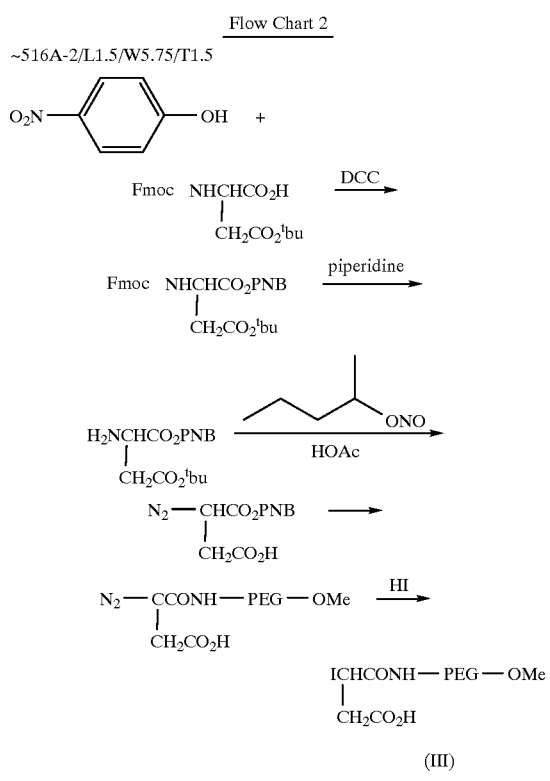

The amino group is converted to the diazonium salt (i-amyl nitrate/HOAc). Displacement of the active PNB ester with $H_2N$-PEG-OMe introduces the polymeric side chain. Treatment with HI results in simultaneous displacement of the diazo linkage with iodide and hydrolysis of the tert-butyl ester protecting group to afford the end result.

If N-protected 3-aminobutyric acid (Flow Chart 3) is utilized in place of Fmoc-N-Asp($^+$bu)OA, the corresponding monofunctionalized iodoacetamide derivative is prepared. Likewise, PEG-iodoacetates are directly prepared by DCC-mediated coupling.

It should be apparent that the linkage of the polymer can be through either an amide or ester. These two functional groups have different susceptability to hydrolysis and the preferred mode of attachment will vary with the specific application. Furthermore, the PEG polymers are available in a variety of molecular weight ranges all of which are potentially useful. Also, the nature of the polymer need not be limited to polyethylene glycol or polypropylene glycol. Other potentially useful polymers include, but are not limited to, polyvinyl alcohol, dextrans and carbohydrates, polypyrrolidone.

Flow Chart 3

~516A-3/L1.5/W5.75/T1.5

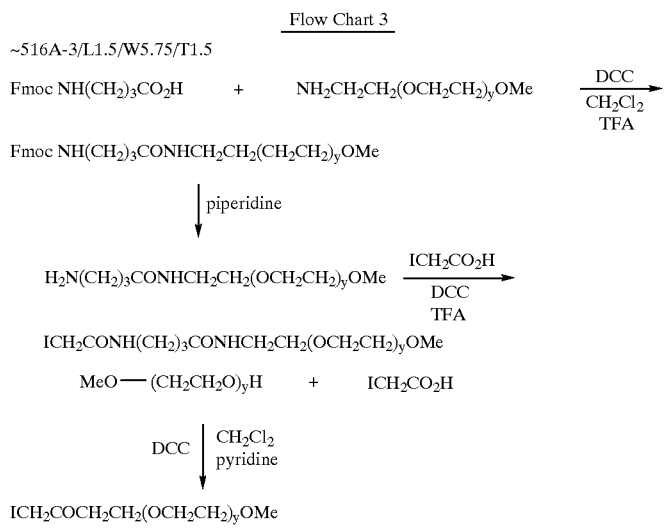

Site Directed Mutagenesis

Preparation of a modified (substituted) recombinant animal (or human) somatotropins or other proteins of this invention can be achieved by site directed mutagenesis. Currently-utilized techniques for the alteration of the DNA sequence of a cloned segment of DNA at a specific defined site require the production of a single stranded form of that DNA. The single stranded DNA is annealed to a synthetic oligonucleotide which is complementary to a portion of it, except that the oligonucleotide contains within it a region of mismatch. The region of mismatch is usually located in the central portion of the oligonucleotide. The annealed mixture is then made double stranded and covalently closed by the addition of E. coli DNA polymerase I, large fragment and deoxynucleotide triphosphates in the presence of T4 DNA ligase and adenosine 5' triphosphate. The double stranded DNA is then transformed into an appropriate E. coli strain where the mismatched region of the DNA is repaired and replicated. Two opulations of clones are obtained. Dependant on which strand is chosen as the template for repair synthesis, a clone either contains the wild type or the altered (mutated) sequence. The clones which contain the mutated sequence, i.e. that which corresponds to the sequence of the oligonucleotide, are selected by hybridisation to the radioactively-labelled oligonucleotide. Due to the mismatch between the oligonucleotide and the wild type sequence, the radioactively-labelled oligonucleotide is more stably bound to the clones which contain the mutated sequence. Incubation at an appropriate temperature therefore differentiates between wild type and mutated clones. The alterations in the identified clones then are confirmed by DNA sequencing of the relevant regions.

One aim of mutagenesis is to generate a preferably-recombinantly-derived procein somatotropin (rpST) somatotropin molecule incapable of the formation of the small loop disulphide bond. The small loop disulphide is located between cysteines at 183 and 191. An additional aim is to incorporate two cysteine residues in the omega loop located at residues 102–112 which has been identified as a site of proteolytic cleavage. These newly incorporated cysteines are further modified using methods described herein. The numbering system is as described. The basic protocol used to obtain the required mutant is hereinafter described.

Substitution of the Ser102 and Tyr112 residues are achieved by using two oligonucleotides. The two oligonucleotides have the following sequence:

5' TTC ACC AAC TGT CTG GTG TTT 3' Ser102 (SEQ ID NO:6)

5' GAC CGC GTC TGT GAG AAG CTG 3' Tyr112 (SEQ ID NO:7)

The template single stranded DNA is pGEM3z-(f+)pST-SX DNA. This single stranded DNA has already been modified to substitute two Glu residues for the cysteines normally found at positions 183 and 191 (This DNA is deposited in an expression vector PR0211, as indicated hereinbelow). 2000 ng of single stranded PGEM3z(f+)pST-SX DNA is mixed with 50 ng of AA1 oligonucleotide, which has previously been 5' phosphorylated with adenosine 5' triphosphate and polynucleotide kinase. The mixture is heated at 65° C. for 7 minutes and then kept at room temperature for 10 minutes. This protocol anneals the oligonucleotide to the single stranded DNA. The annealed DNA is then converted to a double stranded covalently closed form by the addition of ATP, dNTP's (a mixture of the four deoxyribonucleotide 5' triphosphates), T4 DNA ligase and DNA polymerase I large fragment. The mixture is incubated for 1 hour at room temperature. The mixture is then transformed into HB101 COmpetent cells by standard procedures. After overnight incubation at 37° C., colonies are transferred onto nitrocellulose filters and processed for hybridisation by standard protocols. Transformed colonies were identified using a radiolabelled oligonucleotide probe. Plasma DNA is prepared from these colonies, introduced into HB101 competent cell as described previously and rescreened with the radiolabelled oligonucleotide probe. Plasmid DNA is again prepared from colonies which hybridize with the probe. Plasmid DNA from one clone containing the S102C mutation, designated pGEM-3z(f+)pST-SXE-S102C is introduced into JM101 competent cells by transformation and single stranded DNA prepared from purified phage derived from a single transformant.

To mutate the tyrosine at position 112, a second oligonucleotide with following sequence is used:

5' GAC CGC GTC TGT GAG AAG CTG 3' (SEQ ID NO:7)

The process of mutagenesis is identical to that described above except that the template DNA is pGEM-3z(f+)pST- SXE-S102C (this is the clone isolated from the mutagenesis which has the serine at position 102 converted to cysteine) and glutamic acids substituted for cysteines at 183 and 191. The final wash temperature is 56° C. DNA sequencing reveals that the identified clones have the expected sequence. The mutated clone is designated pGEM-3z(f+) pST-SXE-S102C, Y112C.

The altered (mutant) clones are then reconstructed into the bacterial expression plasmid pR0211 (ATCC Accession Number 40483, deposited Aug. 23, 1988) as described in FIG. 5 of EPO publication 173,280. The pGEM clone is cut with EcoRI and HindIII and the pST gene fragment isolated. pR0211 is digested with the same enzymes treated with calf intestinal alkaline phosphatase and the large fragment isolated. The two pieces are ligated together with T4 DNA ligase and transformed into an appropriate bacterial strain, e.g. *E. coli* N99cI deposited.

In this strain a wild type λ repressor is present. This prevents expression from the $P_L$ promoter in pR0211. Once the appropriate construction is isolated, it is then transferred into bacterial strains which contain a temperature sensitive λ repressor, e.g. (ATCC Accession Number 67766, deposted Aug. 23, 1988) *E. coli* 4200. In these strains, the expression of pST is dependent on temperature. At 42° C., the repressor is inactive and expression occurs. At this stage, pST is prepared by procedures contained in EP 173,280 wherein expression occurs (incorporated herein by reference thereto). Expression of pST is not limited to these particular *E. coli* strains. Other strains with appropriate properties are substituted. The plasmid expression vectors are deposited with the ATCC. The bacterial strains are deposited separately.

Other amino acid substitutions can be made by the above procedures utilizing the appropriate codons and oligonucleotides. Similarly, these procedures are employed to modify a variety of animal or human somatotropins.

Method of Use

Advantageously, the novel animal proteins of the present invention are useful for alleviating disease states in animals; improving the growth rate of animals, especially meat producing animals; and increasing the efficiency of feed utilization thereby. Some of these compounds also are effective for enhancing the carcass quality of said animals, i.e. increasing the lean meat to fat ratio of said animals. Moreover, some of the compounds of the present invention are effective for increasing milk production in lactating animals and improving wool production in sheep and other animals raised for coats.

While the derivatized somatotropins of this invention are effective for treatment of animals to achieve the biological improvements described above, that the improved effectiveness and usefulness of the derivatized animal somatotropins of the invention attributed, in part, to the inhibition of aggregation of the somatotropin produced by the derivatization of said somatotropins. Such inhibition permits the preparation of markedly improved sustained release delivery systems which are not readily or effectively achieved with native somatotropins or recombinant somatotropins which are not derivatized as described by the present invention.

It is also found that the derivatized somatotropins of the present invention are highly stable and essentially free of aggregation due to dimer formation. Moreover, the derivatized somatotropins of the invention lend themselves to use in the preparation of significantly improved sustained release compositions.

Where native animal somatotropins have been found to aggregate in a single day, parenteral compositions containing the modified or derivatized somatotropins of this invention continue to release the modified or derivatized somatotropin for 10 days or more.

Compositions

In practice, the compositions of the present invention are generally administered to the animals by injection in the form of biologically active parenteral compositions. Among the parenteral compositions useful for administration of the recombinant animal proteins of this invention are gels, pastes, microspheres, microcapsules, implants and the like. As such, there is considerable interest in providing dosage forms of biologically active substances which release the substance in a controlled manner and thus, reduce the frequency of administration.

The development of sustained release compositions of biologically active macromolecules presents special problems due to their complex modes of action and intricate structures of the macromolecules. Thus, the development of effective sustained release compositions that contain the biologically active somatotropin is required.

The compositions useful for this type of administration are prepared by dissolving the modified or derivatized animal somatotropin in dilute ammonium hydroxide and then adding a solution of an alkali metal benzoate, laurate, carbonate or the like thereto. A nonionic surfactant is thereafter admixed with the solution and the resulting mixture spray dried. The thus formed solids are then admixed with molten fat or wax or a mixture thereof and the resulting molten mixture sprayed through an air/liquid spray nozzle equipped with a heated jacket to maintain the incoming air and the molten phase at a temperature above the melting point. The microspheres are formed as the molten droplets cool. These are collected on a series of sieves in the desired size range of about 45 to 180 microns and retained for use. Microspheres which are not of the desired size range are recycled. Alternatively, the homogeneous mixture is fed onto a centrifugal disc and the microspheres thus formed collected as above, or the molten mixture are cooled and milled to the desired average particle size range.

The biologically active microspheres are then dispersed in a pharmaceutically and pharmacologically acceptable liquid vehicle for injection into the animal. The microsphere-liquid composition is generally administered by subcutaneous injection under the skin of the animal usually in the vicinity of the head, neck or ears.

The derivatized animal proteins of the present invention also are prepared as biocompatible implants which are injected under the skin of the animal using a conventional pellet implant gun. The compositions are prepared by admixing a powdered derivatized somatotropin with a wax such as castor wax or with a mixture of a copoly(glycolide/lactide), magnesium hydroxide, and a condensate of ethylene oxide prepared with a hydrophobic base formed by condensation of propylene oxide with propylene glycol. The thus formed compositions are then introduced into a pelleting press and formed into cylindrical pellets about ⅛ inch in diameter. The thus formed pellets are administered with a conventional pellet implant gun.

The present invention is further illustrated by the examples set forth hereinbelow.

EXAMPLE 1

Preparation of N-Fmoc-Asp($^t$bu)NH-PEG-OMe

To solution of 1.24 g (3 mM) of Fmoc Asp($^t$bu)OH and 40 mL of $CH_2Cl_2$ is added 0.3 g (1.5 mM) of dicyclohexylcarbodiimide and the reaction mixture stirred at room temperature for one hour. The precipitated dicyclohexylurea is filtered off, and 3 g of polyethylene glycol (PEG) amine with an average molecular weight ($^-$Mw) of 2000 is added. The reaction is stirred overnight at room temperature. The methylene chloride is evaporated and the residue dissolved in 300 mL of $H_2O$. This solution was filtered, then ultrafiltered through a YM-2 Amicon membrane and lyophilized to afford 3 g of product.

EXAMPLE 2

Preparation of $H_2N$-Asp($^t$bu)NH-PEG-OMe 3 g of Fmoc-NHAsp($^t$bu)NH-PEG-OMe from Example 1 is added to 30 mL of piperidine-methylene chloride (1:1 v/v) at room temperature and stirred for 30 minutes. The methylene chloride is evaporated and the residue is dissolved in 200 mL of $H_2O$ and ultrafiltered through an Amicon YM-2 membrane. The remaining aqueous solution is lyophilized to yield 2.5 g of product.

EXAMPLE 3

Preparation of $ICH_2CONHAsp$($^t$bu)NH-PEG-OME

To a solution of 0.427 g of iodoacetic acid and 20 mL of methylene chloride is added 0.237 g of DCC and the reaction mixture is stirred at room temperature for one hour. The precipitated dicyclohexylurea is filtered and 2.5 g of $H_2N$-Asp($^t$bu)NH-PEG-OMe is added and the mixture stirred for 3 hours at room temperature (until ninhydrin test is negative). The methylene chloride was evaporated and the residue dissolved in water and ultrafiltered through an Amicon YM-2 membrane. The solution is then lyophilized to yield 2.6 g of product.

EXAMPLE 4

Preparation of $ICH_2CONHAsp$(OH)NH-PEG-OMe 2.6 g of ICH CONH-Asp($^t$bu)NH-PEG-OMe is dissolved in 40 mL of trifluoroacetic acid/methylene chloride (1:1 v/v) and the mixture is stirred at room temperature for one hour. The solvents are evaporated and the residue dissolved in about 200 mL of $H_2O$. The solution is ultrafiltered through an Amicon YM-2 membrane and neutralized at 0° with ammonium hydroxide. Lyophilization affords 2 g of $ICH_2$ CONHAsp(OH)NH-PEG-OMe.

EXAMPLE 5

Preparation of [(MeO-PEG-NHCOAsp(OH) NHCOCH$_2$)Cys$^{183,191}$]-rpST

To a solution of 400 mg of r-pST in 200 mL of 0.5M $NH_4HCO_3$ (pH=8.4) is added 28.0 mg of dithiothreitol and the reaction mixture stirred for 1 hour. To this reduced r-pST is added 1 g of MeO-PEG-NHCOAsp(OH)NHCOCH$_2$I and the mixture allowed to stir for 3 hours. Ellman's test indicates free thiols remain, and so an additional one g of the iodoacetamide derivative was added and the reaction mixture stirred at room temperature for 18 hours. The reaction mixture is diluted, ultrafiltered through an Amicon YM-10 membrane and lyophilized to yield 400 mg of product.

EXAMPLE 6

Preparation of Fmoc NH Asp($^t$bu)COPNB

To a solution of 8 g Fmoc-Asp($^t$bu)OH and 250 mL of methylene chloride is added 2.01 gm of DCC and the resulting solution stirred at room temperature for 1.5 hours. The precipitated dicyclohexylurea was filtered and 1.35 g 4-nitrophenol is added and the reaction mixture stirred for 18 hours. The solution is cooled and washed with cold 5% $Na_2CO_3$ and brine. After drying, the solution is evaporated to yield 4.27 g of product.

EXAMPLE 7

Preparation of $H_2NCH(CO_2PNB)$ $CH_2CO_2^t$bu 2 g of Fmoc NHCH(CO$_2$PNB)CH$_2$CO$_2^t$bu was added to a 30 mL of an ice cold mixture of piperidine and methylene chloride (1:1 v/v) and stirred for 2 hours at 0° C. The soluents were evaporated and the residue redissolved in methylene chloride and washed with cold 0.1N HCl, water and brine. The resulting solution was dried and evaporated to yield 0.83 g of product.

EXAMPLE 8

Preparation of $N_2CH(CONH$-PEG-OMe) $CH_2CO_2^t$bu

A solution of 2.0 g of $H_2NCH(CO_2PNB)CHCO_2^t$bu, 0.91 g i-amyl nitrite, 3 drops of HOAC and 100 mL of $CH_2Cl$ were refluxed for 2 hours. The volatile solvents were evaporated and the residue redissolved in 50 mL of $CH_2Cl_2$ and 5 g of MeO-PEG-NH$_2$ were added. The mixture is stirred evernight at room temperature. The soluents were evaporated and the residue dissolved in $H_2O$ and ultrafiltered through an Amicon YM-2 membrane. Lyophilization yielded 1.48 gm of product.

EXAMPLE 9

Preparation of ICH(CONH-PEG-OMe)CH$_2$CO$_2$H)

A solution of 0.5 g $N_2C(CONH$-PEG-OMe)CH$_2$CO$_2$H is dissolved in 50 mL of CHCl$_3$ and cooled to 0° C. 2 mL of HI is added carefully and the reaction stirred for 30 minutes at 0° C. and then allowed to warm to 28° C. for 2 hours. The solution is evaporated, dissolved in 30 mL $H_2O$ and ultrafiltered through an Amicon YM-2 membrane. After lyophilization 0.3 g of product remains.

EXAMPLE 10

Preparation of [(MeO-PEG-NHCOCH(CH$_2$CO$_2$H) Cys$^{183,191}$)]

To a solution of 500 mg of rpST in 250 mL of 0.5N NaHCO$_3$ (pH=8.4) is added 35 mg of dithiothreitol and the reaction mixture stirred for 1 hour. To the reduced rpST is added 2.0 g of MeO-PEG-NHCOCHI(CH$_2$-CO$_2$H) and the reaction mixture stirred overnight at room temperature. The reaction mixture is diluted with $H_2O$ and ultrafiltered through an Amicon YM-10 membrane and lyophilized to yield 510 mg of product.

EXAMPLE 11

Preparation of MeO-PEG-OCOCH$_2$I

To a solution of 5 g of iodoacetic acid in 250 mL of methylene is added 2.76 g of DCC. The reaction mixture is stirred at ambient temperature for 2 hours and the precipitated dicyclohexylurea removed by filtration. To the remaining solution is added 20 g of MeO-PEG-OH and the reaction mixture stirred overnight at room temperature. The solution is then cooled and transferred to a separation funnel and extracted with 15×10 mL of cold saturated NaHCO$_3$. The remaining methylenechloride solution is evaporated and the residue dissolved in 30 mL of H$_2$O. This solution was ultrafiltered through an Amicon YM-2 membrane and finally lyophilized to yield 5.4 g of product.

EXAMPLE 12

Introduction of Cysteines Into the Omega Loop of Porcine Somatotropin Using Two Synthetic Oligonucleotides A synthetic oligonucleotide designated S102C has the following sequence:

5' TTC ACC AAC TGT CTG GTG TTT 3' (SEQ ID NO:6)

This oligonucleotide differs from the analogous DNA sequence of the rpST gene in that the DNA encoding the serine codon at position 102 is replaced with DNA encoding cysteine. Therefore, the serine present at position 102 is replaced with cysteine.

Singe stranded pGEM-3z(f+)pST-SX DNA is the substrate for mutagenesis. This DNA is composed of a modified rpST gene contained in the commercially available phagemid, pGEM-3z(f+). The modifications of the rpST gene result in the alteration of the DNA sequence to allow for the introduction of a Sac I restriction endonuclease cleavage site at positions 225–230 of the coding region and for the introduction of an Xba I restriction endonuclease cleavage site at positions 285–290. These alterations in the DNA sequence do not change the amino acid sequence of the rpST protein. Two other modifications of the rpST gene result in the alteration of the DNA sequence to allow for the replacement of the cysteine residues at positions 183 and 191 each with glutamic acid. An EcoRI/HindIII fragment containing this modified rpST-SXE gene is cloned into pGEM-3z(f+) DNA cleaved with these restriction endonucleases using standard procedures, resulting in phagemid pGEM-3z(F+)pST-SX. The single stranded pGEM-3z(F+) DNA is prepared from purified phage by standard protocols. 2000 ng of this DNA is mixed with 100 ng of the C183del oligonucleotide, the latter of which has been phosphorylated at its 5' end previously with adenosine 5' triphosphate and polynucleotide kinase. The mixture is contained in a total volume of 10 μl in 1× annealing buffer (1× annealing buffer is 75 mM KCl and 5 mM Tris-Cl, pH 8.0). The mixture is heated at 65° C. for 7 minutes followed by a 10 minute incubation at room temperature. This procedure permits the oligonucleotide to anneal to the single stranded substrate DNA. Annealed molecules are extended and converted to covalently closed, double stranded DNA by the addition of 22 μl H$_2$O, 1 μl 20 mM ATP, 2 units each of T4 DNA ligase, and DNA polymerase I large fragment (for unit definition, see New England Biolabs catalogue, 1986), 2 μl 20× dNTP's (a mixture of the four deoxyribonucleotide 5' triphosphates each at a concentration of 2 mM) and 4 μl 10× fill in buffer (1× fill in buffer is 27.5 mM Tris-Cl pH 7.5, 15 mM MgCl2, 2 mM DTT). After a one hour incubation at room temperature, half of the reaction is introduced into HB101 competent cells by a standard transformation protocol. After overnight incubation at 37° C., colonies are transferred onto nitrocellulose filters and processed for hybridization by standard procedures. oligonucleotide S102C is used for detection of the desired mutation by radiolabelling its 5' end with γ-32P-ATP and polynucleotide kinase. After a three hour prehybridization at 37° C. in 5× SSC, 1× Denhardt's and 150 μg/ml yeast tRNA, the radiolabelled oligonucleotide is added and allowed to hybridize with the DNA on the filters overnight at 37° C. The filters are washed for 30 minutes at 37° C. in 5× SSC, followed by a 30 minute wash in TAC at 58.0° C. During this latter wash, only those colonies whose plasmid DNA contains the desired mutation will continue to hybridize with the radiolabelled oligonucleotide probe. These colonies are detected after exposure of the washed filters to X-ray film. Plasmid DNA is prepared from several of these colonies from the original petri plate, introduced into HB101 competent cells as described previously, and rescreened with the radiolabelled oligonucleotide probe as above. Plasmid DNA is prepared from colonies whose DNA hybridizes with the probe and analyzed for the desired DNA sequence. Plasmid DNA from one clone containing the S102C mutation, designated pGEM-3z (f+)pST-SXE-S102C, is introduced into JM101 competent cells by transformation and single stranded DNA prepared from purified phage derived from a single transformant.

To replace the tyrosine-encoding DNA at position 112 with cysteine-encoding DNA, the following oligonucleotide, designated Y112C, is synthesized:

5' GAC CGC GTC TGT GAG AAG CTG 3' (SEQ ID NO:7)

This oligonucleotide differs from tile analogous DNA in the rpST gene in that the DNA encoding the tyrosine codon at position 112 is replaced by DNA encoding cysteine.

The template single stranded DNA from pGEN-3z(f+) pST-SXE-S102C and Y112C oligonucleotide are annealed, extended and ligated as before. The mixture is introduced into HB101 competent cells and transformants are analyzed for the presence of the mutation exactly as described for S102C. The Y112C oligonucleotide is used as the radiolabelled detection probe. Hybridization and washing conditions are exactly as described for S102C. Several clones containing the Y112C mutation are identified from DNA sequence analysis. Plasmid DNA containing the S102C and Y112C mutations is designated pGEM-3z(f+)pST-SXE-S102C, Y112C.

EXAMPLE 13

Reconstruction Into Appropriate Bacterial Expression Plasmids

The altered (mutant) clones are reconstructed into the bacterial expression plasmid pR0211 (described in EP 173280), incorporated herein by reference thereto. The M13 clones are cut with ECORI and HindIII and the pST gene fragment isolated. pR0211 is cloned with the same enzymes treated with calf intestinal alkaline phosphatase and the large fragment isolated. The two pieces are ligated together with T4 DNA ligase and transformed into an appropriate bacterial strain, e.g. N99cI$^+$. In this strain a wild type λ repressor is present. This prevents expression from the P2 promoter in pR0211. Once the appropriate construction has been isolated, it is then transferred into bacterial strains which contain a temperature sensitive λ repressor, e.g. 4200. In these strains, the expression of rpST is dependent on temperature. At 42° C., the repressor is inactive and expression occurs. At this stage, rpST can be prepared by procedures contained in EP 173280, incorporated herein by reference thereto. The *E. coli* strain which are used for expression of the pST gene product are not limited to *E. coli* 4200. Any appropriate *E. coli* strain can be utilized.

Following the procedures of Examples 1, 2 and 3 above, but substituting the appropriate codons for alanine, serine, glutamic acid, arginine, trypophan, or asparagine for cysteine at positions 183 and 191 converts TGT for cysteine to TCT, AGC or AGT for serine, GAG, or GAA for glutamic acid, CGN, AGA or AGG for arginine, AAT or AAC for asparagine, GCG for alanine, or TGG for tryptophan at said position.

EXAMPLE 14

Preparation of [(MeO-PEG-OCOCH$_2$)Cys$^{102,112}$, Glu$^{183,191}$]-rpST

To a solution of 200 mg of Cys$^{102,112}$ Glu-$^{183,191}$ rpST in 150 mL of 0.5N NaH$_2$O$_3$ (pH=8.4) is added 28 mg of dithrothreital and the solution stirred for 1 hour. To the solution was added 500 mg of MeO-PEG-O$_2$CCH$_2$I ($\overline{M}$w-550) and the reaction mixture stirred for 8 hours at room temperature. The reaction mixture is ultrafiltered through an Amicon YM-10 membrane to yield 135 mg of product.

EXAMPLE 15

Preparation of [(MeO-PEG-NHCOCH$_2$)Cys$^{127}$] Interleukin-2

To a solution of 25 Mg of Interleukin-2 dissolved in 25 mL of 0.5N NaH$_2$O$_3$ (pH-8.4) is added 20 mg of MeO-PEG-NHCOCH$_2$I ($\overline{M}$w-2000) and the reaction mixture stirred for 48 hours until no free thiol is detected. The reaction mixture is ultrafiltered through an Amicon YM-10 membrance to yield 16 mg of product.

EXAMPLE 16

Preparation of [(MeO-PEG-OCOCH$_2$)Cys$^{183,191}$]r-pST

To a solution of 400 mg of rpST in 250 mL of 0.5N NaHCO$_3$ (pH=8.4) is added 28 mg of dithiothreitol and the solution stirred for 1 hour. To the solution is added 1.0 g of MeO-PEG-O$_2$CCH$_2$I ($\overline{M}$w=2000) and the reaction mixture stirred for 6 hours at room temperature. The reaction mixture is ultrafiltered through an Amicon YM-10 membrane and finally lyophilized to yield 420 mg of product.

EXAMPLE 17

Hypox Rat Test Method for Determining the Growth Enhancement of Animals Receiving Derivatized Recombinant Animal Somatotropin The efficacy of various derivatized recombinant animal somatotropins of the present invention in altering the growth rate of animals is determined utilizing the standard hypophysectomized (hypox) rat assay. The hypophysectomized rat does not produce its own growth hormone and is sensitive to injected bovine growth hormone. The response measured is growth over a period of time, such as 10 days.

Each of the hypox albino rats (Taconic Farms, Sprague Dawley-derived) is injected with a sufficient quantity of the compositions prepared in accordance with the Xamples herein to provide a 10-day dose of 800 micrograms (80 micrograms/day) rPST in 0.2 ml of the formulation listed. Alternatively, each of the hypox albino rats is injected daily with 80 micrograms of rPST derivative.

Test Procedures

Prior to the test, the animals are weighed and the animals to be used for the test are selected based on body weight. Only those animals whose body weights are one standard deviation from the mean body weight of the group are selected. The resulting group is then randomly divided into treatment groups consisting of eight rats/group by a computer generated randomization procedure. The test animals are then transferred to a clean cage and housed four rats/cage. On the initial day of the study the test animals are weighed and any animals with excessive weight gain or loss (±5 grams) are replaced. The animals are then assigned to test groups and treated.

At the end of the ten-day test period, total weight gain for each animal is recorded and the average weight gain per rat for each treatment determined. The results of these experiments, which are summarized in Table I below, demonstrate the bioactivity of these derivatives.

TABLE I

Hypox Rat Test

Hypox Rat Data

| derivative | PEG $\overline{M}$w | gms (growth) | | | | |
|---|---|---|---|---|---|---|
| | | 0–2 days | 2–4 days | 4–7 days | 7–10 days | total |
| [[(MeO—PEG—O$_2$CCH—(CH$_2$CO$_2$Na$^+$)NHCO—CH$_2$]Cys183,191]-r—pST | 2000 | 8.6 | 6.3 | 9.0 | 7.5 | 31.4 |
| [(MeO—PEG—O$_2$C—CH$_2$)Cys183,191]-r—pST | 5000 | 8.8 | 5.0 | 10.3 | 7.3 | 31.3 |
| [(MeO—PEG—O$_2$C—CH$_2$)Cys183,191]-r—pST | 2000 | 9.8 | 4.8 | 8.9 | 5.9 | 29.3 |
| r—pST | — | 6.9 | 5.3 | 6.8 | 9.0 | 28.0 |

From the above data it is seen that each of the derivatized recombinant porcine somatotropins evaluated is biologically active and provides excellent growth of animals.

EXAMPLE 18

Stability Profiles of Modified or Derivatized Recombinant Animal Somatotropins

A concentrated solution of the recombinant animal somatotropin derivative (up to 100 mg/ml) in phosphate buffered saline pH 7.4 (NaH$_2$PO$_4$H$_2$O 3.45 gm, Na$_2$HPO$_4$ 3.55 gm, NaCl 9.50 gm dissolved in distilled water to 1000 ml) is prepared. This is filtered through a millipore sterile Millex-0.22 um filter unit and 0.1 ml aliquots placed into tubes. These are placed in a 45° C. oven and removed at the required intervals. The contents are then diluted with phosphate buffered saline. The supernatent is assayed for monomer and dimer content by HPLC. A mass balance is done; any precipitated material is recorded. Results are compared with the initial concentrations, and a stability profile documented.

Alternately, a somatotropin derivative exhibiting poor solubility at pH 7.4 is dissolved at a less preferred pH (4–10) or is evaluated as a suspension (see Table II).

TABLE II

| Sample | 7 days Fraction Soln. (Dimer) | 14 days Fraction Soln. (Dimer) | 21 days Fraction Soln. (Dimer) |
|---|---|---|---|
| [(MeO—PEG—OCO$_2$CH$_2$)Cys$^{183,191}$]r-pST | | | |
| $\overline{M}$W = 2000 | 52 | — | — |
| $\overline{M}$W = 5000 | — | 19 | — |

TABLE II-continued

| Sample | 7 days Fraction Soln. (Dimer) | 14 days Fraction Soln. (Dimer) | 21 days Fraction Soln. (Dimer) |
|---|---|---|---|
| [(MeO—PEG—NHCO) (CO$_2^-$Na$^+$)CHNHCOCH$_2$]Cys$^{183,191}$ r-pST MW = 200 | | | 83 |
| r—PST technical | 85.9 (29.4) 89.5 (31.0) | 65.4 (45.5) 64.0 (44.9) | 59.8 (51.7) 57.9 (49.2) |

EXAMPLE 19

Preparation of Implants Using [(MeO-PEG-O$_2$CCH$_2$)Cys$^{183,191}$] rpST and Evaluation of Said Implants by in vitro Dissolution A set of implants are prepared from 96 mg of –270 mesh castorwax and 64 mg of powdered [(MeO-PEG-O$_2$CCH$_2$)Cys$^{183,191}$]rpST and rpST. The average molecular weight of the PEG is 2,000. The mixture is agitated, poured over a large surface petri dish and the CH$_2$Cl$_2$ allowed to evaporate at room temperature and then dried by vacuum drying. The dried residue is collected and formed in ⅛" diameter cylindrical implants using a Carver Press at about 1000 psig. The thus-formed implants weigh 60 to 70 mg each. The thus-prepared implants are then subjected to an in vitro dissolution evaluation. Each of the implants is placed in a separate plastic tube containing 10 ml of a phosphate buffer solution (ph 7.4 with 0.05% Na azide) and the tubes placed in a shaking water rack where the tubes are shaken while the temperature of the water in the unit is maintained at 39° C. The tubes are shaken for one day, then the solutions removed from each tube and analyzed for rpST by HPLC and the solution discarded. New phosphate buffer solution is added to each tube and the tubes shaken for three additional days thereafter. The solutions from each tube is again analyzed for rpST by HPLC and (the solution again is discarded). New phosphate buffer are again added to each tube and the tube again shaken for three days then analyzed again for rpST.

The phosphate buffer solution is (NaH$_2$-PO$_4$.H$_2$O 3.45 g, Na$_2$HPO$_4$ 3.55 g, Nacl 9.5 g dissolved in distilled water to 1000 ml (see Table III).

TABLE III

Implant Release
Implants pressed from a mixture of 60% Castorwax and 40% r-pST and coated with silicone tubing

| Compound | PEG Mw | % Released Day 1 | Day 4 | Day 7 |
|---|---|---|---|---|
| r-pST | | 8.1 | 11.3 | 12.9 |
| [(MeO—PEG—OCCH$_2$)—Cys$^{183,191}$]pST | 2000 | 12.4 | 17.1 | 17.6 |

EXAMPLE 20

Construction of an Expression Plasmid

A synthetic gene encoding the 155 amino acid form of human bFGF (Abraham, J. A., et al, EMBO J. 5: 2523–2528 (1986)) cloned into pUC 18 was purchased from British Bio-technology, Oxford, UK. Destruction of the internal NcoI restriction site at positions –2 to 3, which includes the N-terminal methionine codon of the bFGF cDNA, and introduction of a unique NdeI site is as follows. The nucleotide sequence (–12 to 36) to be changed (a, below) is excised from pUC 18 with HindIII and BspMII and a synthetic fragment (b, below) containing an internal NdeI site cloned into pUC 18. This cloning results in a construct that contains a 4 nucleotide deletion in the upstream non-coding region compared to the original construct (see below). This deletion has no effect on the relative protein yields of bFGF using the expression system described below.

5' AGCTTACCTGCC<u>ATG</u>GCAGCCGGGAGCATCACCACGCTGCCCGCCCTT 3' (a) (SEQ ID NO:8)

5' AGCTTCAT<u>ATG</u>GCAGCCGGGAGCATCACCACGCTGCCCGCCTT 3' (b) (SEQ ID NO:9)

Only the sense strands are shown for the original (a) and modified (b) fragments, respectively. The codon underlined indicates the position of the methionine start codon.

The cDNA encoding bFGF is then excised from pUC 18 with NdeI and BamH1 and cloned into the Nde1 and BamH1 sites of the expression vector pT7 Kan 5, derivative of pET-3a (plasmid for Expression by bacteriophage T7, as defined in Rosenberg, A., et al, Gene 56: 125–135 (1987) at page 128) containing the T7 promoter for RNA polymerase.

EXAMPLE 21

Construction of GLU$^{3,15}$ hbFGF

The protocol for the construction of glu$^{3,5}$hbFGF is identical to that described above for the introduction of the NdeI restriction site except that the region encoding the first 5-terminal amino acids of basic FGF (c) are changed to encode those of acidic FGF (d):

5' AGCTTCATATGGCAGCCGGGAGCATCAC-CACGCTGCCCGCCCTT 3' (c) (SEQ ID NO:10)

5' AGCTTCATATGGCT<u>GAA</u>GGG<u>GAA</u>ATCACCACGCTGCCCGCCCTT 3' (d) (SEQ ID NO:11)

Only the sense strands are shown for the original (c) and modified (d) fragments, respectively. The codons underlined indicate those changed to encode glutamic acid at positions 3 and 5.

EXAMPLE 22

Expression of Glu$^{3,5}$ Mutants

Following sequence verification (Sanger, F., et al., Proc. Nat. Acad. Sci. 74:5463–5467 (1977)), the genes encoding the bFGF mutants are transformed into competent BL21 pLysS cells. E. coli cells harboring the plasmids are grown in Luria broth containing kanamycin sulfate (50 μg/ml or ampicillin (100 μg/ml) for plasmid pET3a (ML3), a derivative of pET 3a glu$^{3,5}$ hbFGF and chloramphenicol (34 μg/ml) at 37° C. to about 0.6 absorbance units at 600 nm. bFGF synthesis is induced by addition of isopropyl-beta-D-thiogalactopyranoside (1 mM). Two hours postinduction, the cells are then harvested by centrifugation at 4° C.

EXAMPLE 23

Purification of glu$^{3,5}$ hbFGF Mutants

Cell pellets from 1 liter cultures are resuspended in 30 ml 50 mM Tris, 0.1 mM EDTA buffer, pH 7.6, and lysed by 3 rapid freeze/thaw cycles. The lysate is then treated with DNase I (20 μg/ml) in the presence of 5 mM $MgCl_2$ for 20 min at 4° C. and centrifuged at 10,000×g for 20 min to remove cell debris. bFGF activity is found to be equally distributed in the pellet and supernatant fractions.

bFGF is purified from the supernatant solution by heparin-sepharose column chromatography as described by Gospodarowicz, D., et al., Proc. Nat. Acad. Sci. USA 81:6963–6967 (1984), and eluting with a linear salt gradient from 0.6 to 3.0M NaCl. The fractions containing growth factor are pooled and diluted with 10 mM, pH 7.6 Tris buffer to give a final NaCl concentration of about 0.6M.

This is loaded onto a 0.75×7.5 cm TSK Heparin-5PW column (TosoHaas, Philadelphia, Pa.) equilibrated with 10 mM, pH 7.6 Tris, 0.6M NaCl. Elution of bound material is monitored at 280 nm and is accomplished using a linear salt gradient (0.6 to 3.0M NaCl in 60 min) at a flow rate of 0.7 ml/min.

Using the T7 expression system described in Example 4, the yield of native sequence hbFGF (2–155) is about 0.8 mg/l bacterial culture. With native sequence haFGF, a 6 to 8 mg/liter yield is obtained. $Glu^{3,5}$hbFGF expressed in the same system gives 8 to 10 mg/liter of purified factor.

EXAMPLE 24

Characterization of hbFGF and $glu^{3,5}$ hbFGF Mutants (a) Chromatographic Behavior Heparin HPLC purified bFGF's are analyzed by reverse phase high performance liquid chromatography, RP-HPLC ($C_4$, Vydac, the separations Group, Hesperia, CA) using a 0.1% trifluoroacetic acid/acetonitrile gradient (0 to 28% $CH_3CN$ in 15 min, 28–60% in 99 min, and 60 to 30% in 10 min) at a flow rate of 0.7 ml/min. Elution of bound material is monitored at 210 nm.

The elution profile from heparin sepharose chromatography of a crude cell homogenate containing native sequence hbFGF (2–155) shows two major protein peaks both of which possess mitogenic activity and contain a major protein species of $M_r$ 17,000 by sodium dodecyl sulfate polyacrylamide gel electrophoresis (SDS-PAGE). $C_4$ reverse phase-high performance liquid chromatorgaphy (RP-HPLC) of material from each of the two peaks obtained from the heparin sepharose step followed by N-terminal sequence analysis of the resolved components identify at least 3 distinct forms of bFGF.

As a first approach to analyze this apparent microheterogenetity, the contribution of thiol-disulfide interchange (disulfide scrambling) in the generation of chromatographically distinct species is assessed by treatment with a reducing agent. Incubation of a portion of heparin sepharose purified bFGF with dithiothreitol (2 mM) for 10 min at 37° C. followed by RP-HPLC analysis shows that the peaks previously identified as bFGF species chromatograph essentially as a single peak.

Figure 2:
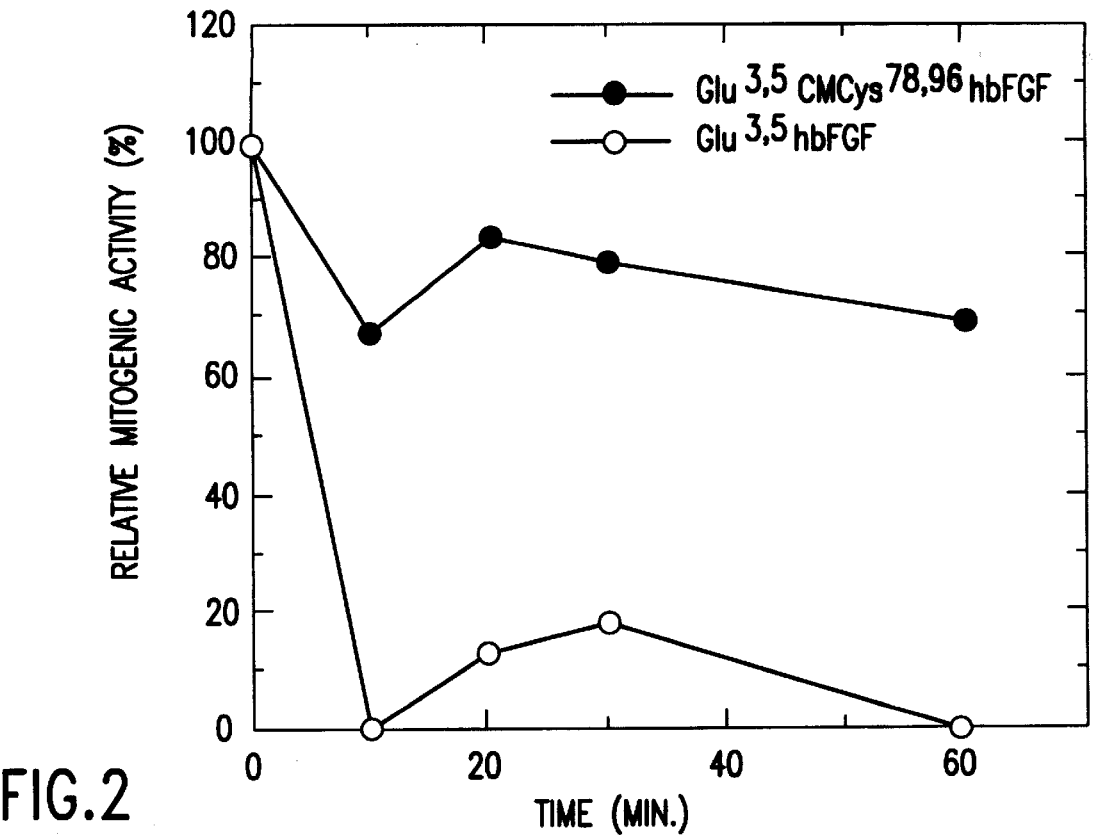
Figure 3:
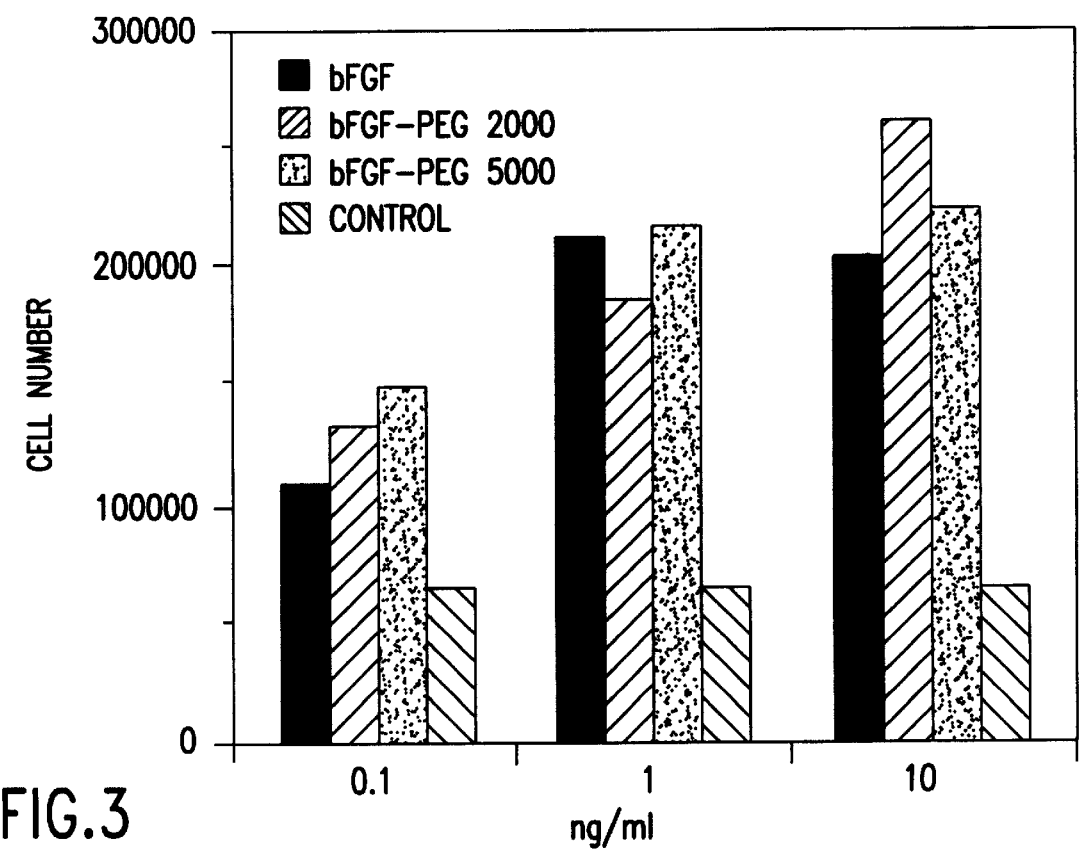

High resolution TSK Heparin HPLC of 2 protein peaks containing FGF from the heparin sepharose step reveals 4 major protein components that elute over a range of 1.6 to 2.3M NaCl (FIG. 2). Analysis by SDS-PAGE of these peaks shows P-I, P-III and P-IV to contain a single protein band that migrates with an $M_r$ of 17,000 consistent with that hbFGF(2-155), whereas PII exhibits an $M_r$ of about 22,000 and is identified by N-terminal sequence analysis as a contaminant. Treatment of a portion of the pooled material from heparin sepharose chromatography with dithiothreitol (5 mM) for 10 min at room temperature followed by heparin HPLC shows an increase in the amount of P-I, a reduction in that of P-III and the disappearance of P-IV; the position and intensity of P-II containing the $M_r$ 22,000 impurity is unaffected by this treatment (FIG. 3).

The chromatographic behavior of the $glu^{3,5}$hbFGF in the presence and absence of dithiothreitol on heparin and RP-HPLC is similar to that observed for native sequence hbFGF.

(b) Sequence Analyses

N-terminal sequence analyses of reverse phase purified proteins are performed on a model 477A pulsed-liquid phase sequencer (from Applied Biosystems, CA) equipped with an on-line phenylthiohydantoin- amino acid analyzer (Model 120A, Applied Biosystems, CA). Amino acid compositions are determined after HCl gas phase hydrolysis (5.7M HCl/ 0.1% phenol; 24 h at 110° C.) using a model 420A phenylisothiocyanate-derivatizer equipped with an on-line model 130A separation system (Applied Biosystems, CA).

N-terminal sequence analysis of the material isolated from heparin HPLC gives a single sequence consistent with $glu^{3,5}$hbFGF (2–155) indicating complete removal of the N-terminal methionine.

(c) Molecular Weights

Molecular weight determinations are performed on a 10 to 15% gradient and 20% homogeneous polyacrylamide gels in the presence of sodium dodecyl sulfate (SDS-PAGE) using a silver stain detection system (Phastgel System, Pharmacia/ LKB). hbFGF (2–155) migrates with an $M_r$ of 17,000 compared to an $M_r$ value of about 19,000 for $glu^{3,5}$hbFGF. Molecular weights calculated from amino acid sequence data for hbFGF and the chimeric version are 17,124 and 17,224, respectively. To resolve the apparent molecular weight discrepancy, a sample of $glu^{3,5}$hbFGF is analyzed by liquid-secondary ion mass spectrometry and gives a molecular ion of mass 17,365. This value is, within experimental error, consistent with that predicted from sequence data. While not wishing to be bound to any theory, the anomalous migration of $glu^{3,5}$ on polyacrylamide gels under denaturing conditions is most likely due to interference of protein-SDS interactions from the glutamyl side chains at positions 3 and 5.

EXAMPLE 25

Bioassay of Native and Mutant hbFGF Derivatives

The mitogenic activity of native sequence hbFGF and mutants is determined using bovine vascular endothelial cells derived from adult aortic arch as described by Esch, et al., Proc. Nat. Acad. Sci. USA 82: 6507–6511 (1985). Cells are seeded at the initial density of 0.8×104 cells per 24-well plate in 0.5 ml Dulbecco's modified Eagle's medium (DMEM) containing 10% calf serum (Hyclone, Logan, UT) supplemented with penicillin (100 units/ml), streptomycin (100 μg/ml) and L-glutamine (2 mM). Two hours after plating, 20 μl-aliquots of appropriate dilutions (0.001 to 100 ng/ml) of bFGF in DMEM containing 0.5% bovine serum albumin (BSA) are added. After 5 days in culture, duplicate plates are trypsinized and cell densities determined by cell counting in a Coulter counter.

Alternatively, growth curves in the presence and absence of bFGF are determined by measuring acid phosphatase levels after cell lysis using p-nitrophenyl phosphate as substrate (Connolly, D. T., et al., Anal. Biochem. 152:136–140 (1986), page 137). Cells are seeded at an initial cell density of 1000 to 1200 cells per well (0.32 $cm^2$, 0.64 cm diameter flat bottomed 96 well plates) in 0.25 ml DMEM containing 10% calf serum, antibiotics and L-glutamine.

After plating, 10 μl-aliquots of appropriate dilutions of growth factor (0.001 to 100 ng/ml) in DMEM containing 0.5% BSA are added.

After 4 to 5 days in culture, each well is washed and 100 μl pH 5.5 buffer containing 0.1M sodium acetate, 0.1% Triton X-100 and 10 mM p-nitrophenyl phosphate (Sigma 104 phosphatase substrate) are added to each well. The plates are incubated at 37° C. for 2 hours, the reaction stopped by adding 10 μl of 1N sodium hydroxide, and color development determined at 405 nm against a buffer blank incubated without cells using a UV max kinetic microplate reader (Molecular Devices, CA). Determinations are made in triplicate. Both methods give indistinguishable dose-response curves.

When the mitogenic properties of recombinant hbFGF and mutant proteins are compared to those of bFGF (10–155) originally isolated from bovine brain, human recombinant bFGF and glu$^{3,5}$hbFGF show a dose-dependent stimulation of endothelial cell growth that is essentially identical to that for bovine brain bFGF (FIG. 5) and exhibit doses for half-maximal stimulation (median effective dose, $ED_{50}$) of 0.3 to 1.0 ng/ml and a maximal stimulation between 3 and 10 ng/ml.

BalbC 3T3 cells are grown in Dulbecco's modified Eagle's medium (DMEM) supplemented with 10% fetal calf serum, trasferrin (10 μg/ml), penicillin (100 units/ml) and streptomycin (100 μg/ml). On day 1, trypsin- dispersed cells are plated into 24-multiwell plates at 50,000 cells/well in the above media. On day 2 the medium is replaced with DMEM containing 0.5% fetal calf serum. On day 3 the cells are washed with 1 ml serum-free DMEM and 0.5ml DMEM containing 0.4 μCi/well tritiated thymidine is added. Experimental samples are then added to the wells in a volume not greater than 20 μl. After 24 h, the cells are placed at 4° C., washed (3×1 ml) with phosphate buffered saline (PBS), and 1 ml of 5% trichloroacetic acid is added. After 30 min, the cells are washed with PBS (3×1 ml); 0.5 ml 0.5M NaOH is added and the cells incubated at room temperature for 30 min. Radioactivity in duplicate samples (100 μl) from each well is then determined by liquid scintillation counting.

The binding of $^{125}$I-bFGF to baby hamster kidney (BHK) cells is essentially as described (Moscatelli, D., J. Cell. Physiol. (1987)131, 123–130). Briefly, cells are grown in Dulbecco's modified Eagle's medium (DMEM) supplemented with 5% fetal calf serum and 5% calf serum. Cells are plated into 24 multiwell plates at about $10^5$ cells/well and incubated overnight. The cells are washed once with 0.5 ml PBS and incubated at room temperature in 0.5 ml DMEM containing 25 mM HEPES buffer, pH 7.5, 0.15% gelatin. After 15 min the medium is replaced with fresh medium and $^{125}$I-bFGF (50 pmol) and unlabelled bFGF analogs added in a volume not greater than 50 μl. Plates are then incubated at room temperature on an orbital shaker for 1 h followed by a 1 h incubation at 4° C. At the end of the incubation, cells are washed with 0.5 ml ice cold PBS and 20 mM HEPES buffer, pH 7.5 containing 2M NaCl (2×0.5 ml) and then solubilized by incubation (30 min, 4° C.) in 0.5 ml 0.5% Triton X-100 in 0.1M sodium phosphate, pH 8. Radioactivity present in the incubation medium, 2M NaCl wash and the Triton X-100 extracts are determined in duplicate by gamma scintillation counting.

The above description is for the purpose of teaching the person of ordinary skill in the art how to practice the present invention and it is not intended to detail all those obvious modifications and variations of it which will become apparent to the skilled worker upon reading the description. It is intended, however, that all such obvious modifications and variations be included within the scope of the present invention as defined in the appended claims.

The DNA sequences, plasmids and/or microorganisms deposited in connection with the present patent application, except where specified to the contrary, are deposited in American Cyanamid Company's culture collection maintained in Pearl River, New York and are available to the public when legally appropriate to do so. Further, the following are deposited additionally with the American Type Culture Collection (ATCC), 10801 University Boulevard, Manassas, Virginia 20110-2209 USA. on the date indicated with the ATCC accession numbers indicated:

BL21 lys-S/pET glu$^{3,5}$hbFGF deposited on Nov. 13, 1990 with ATCC No. 68477.

The above contain the DNA of glu$^{3,5}$hbFGF as described herein.

EXAMPLE 26

Derivatives with MeO-PEG Compounds

Glu$^{3,5}$hbFGF (2–155) is prepared as described hereinabove. Polyethylene glycol iodoacetates (meo-PEG-O$_2$-CCH$_2$I; MW=2000 and 5000) and iodoacetamide (MeO-PEG-NHCOCH$_2$I; MW=5000) are prepared as described herein.

Glu$^{3,5}$hbFGF (5 mg/ml) in 0.1M Tris buffer pH8.6 containing 2 mM EDTA is reduced by addition of dithiothreitol (5MM) and incurbated for 1 h at room temperature under an argon atmosphere. MeO-PEG-O$_2$-CCH$_2$I (MW=2000 or=5000) MeO-PEG-NHCOCH$_2$I (MW=5000) is added to give a final concentration of 25–50 mM and the reaction mixture is then dialysed against phoshate buffered saline (PBS) at 4° C. for 12 h.

EXAMPLE 27

Derivatized FGF

Glu$^{3,5}$hbFGF(5 mg/ml in 10 mM Tris buffer pH7.4 containing 1.5M Nacl is reduced by addition of dithiothreitol (5 mM) and incubated for 0.5–1 h at room temperature under an argon atmosphere. Iodoacetic acid (0.4M in 1M Tris buffer pH8.5) is then added to give a final concentration of 50 mM and the reaction mixture incubated in the dark for 2 h at room temperature. The solution is then dialysed against 10 mM Tris buffer (pH 7.0) containing 0.5M NaCl for 12 h.

Both the polyethylene glycol derivative of bFGF and the carboxymethylated bFGF are assayed as described hereinabove.

EXAMPLE 28

Carboxymethylated FGF

Carboxymethylated bFGF: Treatment of Glu$^{3,5}$hbFGF (2–155) with iodoacetic acid under non-denaturing conditions results in the carboxymethylation of 2 of the 4 cysteine residues of bFGF. The positions of modified cysteines are identified as cysteine 78 and 96 by peptide mapping of a endoproteinase Glu-C digest of $^{14}$C-labelled carboxymethylated bFGF. Modification of cysteine 78 and 96 has no effect on the affinity of bFGF for heparin. The mitogenic activity and receptor binding properties of Glu$^{3,5}$CMcys$^{78,96}$hbFGF are indistinguishable from that of Glu$^{3,5}$hbFGF (FIG. 1) whereas fully carboxymethylated bFGF does not seem active. In contrast to unmodified bFGF,Glu$^{3,5}$hbFGF has a half-life at pH 4 of about 5 min, whereas that for Glu$^{3,5}$CMCys$^{78,96}$hbFGF is >60 min (see FIG. 2).

Polyethylene glycol esters of bFGF: PEG-2000 and −5000 derivatives of Glu$^{3,5}$hbFGF are fully active in bovine endothelial cell mitogenic assays (FIG. 3) and bind to heparin. PEG ester derivates undergo hydrolysis to give carboxymethylated bFGF, a stabilized and fully active analog (see Example 24), which may be monitored by the appearance of an 18 Kd protein (glu$^{3,5}$CMcys$^{78,96}$hbFGF) on sodium dodecyl sulfate polyacrylamide gels.

Polyethylene glycol amide of bFGF: PEG-5000 derivative of glu$^{3,5}$hbFGF in contrast to the PEG esters of bFGF are stable. They are fully active in BalbC 3T3 fibroblast mitogenesis assays and compete as effectively as unmodified glu$^{3,5}$hbFGF in FGF receptor binding assays.

BIBLIOGRAPHY

1. Abraham, J. A., et al., EMBO J. 5: 2523–2528 (1986).
2. Arakawa, T. and Fox G. M., Eur. Pat. Ap. No. 320,148 (1989).
3. Barr, P. J., et al., Biol. chem. 263: 16471–16478 (1988).
4. Bergonzoni, L., et al., Eur. Pat. Ap. Pub. No. 363,675 (1989).
5. Burgess, W. H., and Maciag, T., Ann. Rev. Biochem. 8: 575–606 (1989).
6. Connolly, D. T., et al., Anal. Biochem. 152: 136–140 (1986).
7. Davidson, J. M., et al., J. Cell Bio. 100: 1219–1227 (1985).
8. Esch, F., et al., Proc. Nat. Acad. Sci. USA 82: 6507–6511 (1985).
9. Esch, F., et al., Eur. Pat. Ap. Pub. 228,449 (1986).
10. Fiddes, J. C., et al., Eur., Pat. Ap. Pub. No. 298,723 (1989).
11. Franco, W. P., U.S. Pat. No. 4,296,100 (1981).
12. Franco, W. P., U.S. Pat. No. 4,378,347 (1983).
13. Abraham, J. A., et. al., EMBOJ5:2523–2528 (1986).
14. Rosenberg, A., et. al., Gene 56: 125–135 (1987).
15. Sanger, F. et. al., Proc. Nat. Acad. Sci. 74: 5463–5467 (1977).
16. Gospodarowicz, D., et. al., Proc. Nat. Acad. Sci. USA 81:6963–6967 (1984).
17. Esch, et. al. Proc. Nat. Acad. Sci. U.S.A. 82: 6507–6511 (1985).

What is claimed is:

1. A derivatized basic fibroblast growth factor protein or polypeptide wherein at least one cysteine residue of said protein or polypeptide is derivatized with a substituent selected from the group consisting of: $CH_2CO_2R_1$, $CH_2CONHR_1$, $CH(COR_2)_x(CH_2)_x(COR_3)$, $CH_2CONHCH(COR_2)(CH_2)_x(COR_3)$ and $CH_2CONH(CH_2)_x(COR_4)$; wherein $R_1$ is $CH_2CH_2(OCH_2CH_2)_yOMe$; $R_2$ and $R_3$ are OH or $R_4$; $R_4$ is $NHCH_2CH_2(OCH_2CH_2)_yOMe$ or $OCH_2CH_2(OCH_2CH_2)_yOMe$; x is an integer of from 1 to 3 and y is an integer of from 10 to 300; with the provisos that $R_2$ and $R_3$ cannot simultaneously be OH; and that, when two derivatized cysteine residues of said protein or polypeptide form a disulfide linkage prior to derivatization, both cysteines will bear the same sulfhydryl derivative.

2. The protein or polypeptide according to claim 1, wherein said protein or polypeptide contains at least one cysteine residue in its natural form.

3. The protein or polypeptide according to claim 1, wherein said protein or polypeptide has an additional or substituted cysteine residue in the natural form of the protein or polypeptide.

4. The protein or polypeptide according to claim 2, wherein said fibroblast growth factor is $Glu^{3,5}hbFGF$.

5. A pharmaceutical composition comprising a pharmacologically effective amount of the derivatized protein or polypeptide of claim 1 or a pharmaceutically acceptable salt thereof and a pharmaceutically acceptable solid or liquid carrier.

6. The composition according to claim 5, wherein said composition contains a liquid carrier which is suitable for parenteral administration to an animal.

* * * * *